US008815311B2

(12) United States Patent
Heaton et al.

(10) Patent No.: US 8,815,311 B2
(45) Date of Patent: Aug. 26, 2014

(54) METHODS FOR IMPROVING THYROID FUNCTION IN A SUBJECT

(71) Applicant: Quality IP Holding, Inc., Carson City, NV (US)

(72) Inventors: Amy L. Heaton, Salt Lake City, UT (US); Mitchell K. Friedlander, Salt Lake City, UT (US); Dennis Gay, Salt Lake City, UT (US)

(73) Assignee: Quality IP Holdings, LLC, Carson City, NV (US)

( * ) Notice: Subject to any disclaimer, the term of this patent is extended or adjusted under 35 U.S.C. 154(b) by 0 days.

(21) Appl. No.: 13/623,116

(22) Filed: Sep. 20, 2012

(65) Prior Publication Data
US 2014/0079830 A1 Mar. 20, 2014

(51) Int. Cl.
A61K 36/55 (2006.01)
A61K 36/00 (2006.01)
A61K 47/00 (2006.01)
A61K 9/14 (2006.01)
A61K 9/00 (2006.01)

(52) U.S. Cl.
USPC ........... 424/745; 424/725; 424/774; 424/439; 424/489; 424/400

(58) Field of Classification Search
None
See application file for complete search history.

(56) References Cited

PUBLICATIONS

Fung et al. (2002) J. Clin. Pharmacol. 42: 30-36.*
Website document entitled "Growth Hormone: Amino Acids as GH Secretagogues" (available at http://www.vrp.com/amino-acids/growth-hormone-amino-acids-as-gh-secretagogues-a-review-of-the-literature?utm_source=RSStwitterfeed&utm_medium_=twitter) Downloaded from website Apr. 8, 2013.*
Ho et al. (1989) Clinical Endocrinology 30, 335-345.*
Website document entitled "Schizonepeta Tenuifolia" (available at http://examine.com/supplements/Schizonepeta+Tenuifolia). Downloaded from website Nov. 21, 2013.*
Grunfeld et al. (1988) J. Clinical Endocrinology and Metabolism vol. 67, No. 5, pp. 1111-1114.*
Salomon et al. (1989) New England J. Med. vol. 321, No. 26, pp. 1797-1803.*
Moller et al. (1992) Metabolism, vol. 41, No. 7, pp. 728-731.*
Reid et al. (1994) J. Clin. Invest. vol. 94. pp. 2468-2474.*
Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 11861189.

Albert et al.; Low-Dose Recombinant Human Growth Hormone as Adjuvant Therapy of Lifestyle Modifications in the Management of Obesity; Journal of Clinical Endocrinology & Metabolism 89(2) 695704; 2004.
Bernardi et al.; Somatotropic axis and body weight in premenopausal and post-menopausal women: evidence fora neuroendocrine derangement, in absence of changes of insulinlike growth factor binding protein concentrations; Human Reproduction vol. 12, No. 2 pp. 279-287, 1998.
Bidlingmaier et al.; Growth Hormone; Handbook cf Experimental Pharmacology 195; 2010; pp. 187-200.
Bjorntorp, et al.; Hypothalamic Origin of the Metabolic Syndrome X; Annals New York Academy of Sciences, pp. 297 307; 1999.
Bjorntorp, P.; Do Stress reactions cause abdominal obesity and comorbidities?; The International Association for the Study of Obesity, Obesity reviews; 2 73-85; 2001.
Bjorntorp, P.; The regulation of adipose tissre distribution in humans; International Journal of Obesity (1996) 20, 191302.
Blackman et al.; Growth Hormone and Sex Steroid Administration in Healthy Aged Women and Men A Randomized Controlled Trial; JAMA, Nov. 12, 2002—vol. 288, No. 18; pp. 2282-2292.
Bredella, et al.; Peak Growth Hormone-Releasing Hormone-Arginine-Stimulated Growth Hormone iS Inversely Associated with Intramyocellular and Intrahepatic Lipid Contentin Premenopausal Women with Obesity; J. Clin Endrocrinol Metab. Oct. 2009; 94(10): 3995-4002.
Carli et al.; Changes in the exercise-induced hormone response to branched chain amino acid administration; Eru. J. Apl. Physiology (1992) 64:272-277.
Chromiak et al.; Use of Amino Acids as Growth HormoneReleasing Agents by Athletes; Nutrition 18:657-661, 2002.
Cooper et al., Subclinical thyroid disease; Published Online Jan. 23, 2012 13 pages.
Corpas et al.; Human Growth Hormone and Human Aging; Endocrine Reviews, vol. 14, No. 1; 1993; pp. 2039.
Corpas et al.; Oral Arginine-Lysine Does not Increase Growth Hormone or Insulinlike Growth Factor-I in Old Men; Journal of Gerontology: 1993, vol. 48, No. 4, M128-M133.
Ding et al.; Novel serum protein biomarkers indicative of growth hormone doping in healthy human subjects; Preteomics 2011, 11, 3565-3571.
Fogelholm et al. Low-Dose Amino Acid Supplementation: No Effects on Serum Human Growth Hormone and Insulin in Male Weightlifters; International Journal of Sport Nutrition, 1993, 3, 290-297.
Gourmelen et al., Effet du chlorhydrate d'ornithine sur le taux plamatique de l'hormone de croissance (HGH); Annels D'Endocrinologie; pp. 526-528; 1972.
Hayes et al.; Recombinant Human Growth Hormone and Recombinant Human InsulinLike Growth Factor I Diminish the Cataboloic Effects of Hypogonadism in Man: Metabolic and Molecular Effects; The Journal of Clinical Endocriology & Metabolism; vol. 86, No. 5; 2001.

(Continued)

Primary Examiner — Chris R Tate
Assistant Examiner — Russell Fiebig
(74) Attorney, Agent, or Firm — TraskBritt

(57) ABSTRACT

Embodiments of the invention generally relate to methods for improving thyroid function in healthy human beings.

14 Claims, No Drawings

(56) References Cited

PUBLICATIONS

Hersch et al.; Growth hormone (GH)-releasing hormone and GH secretagogues in normal aging: Fountain of Youth or Pool of Tantalus?; Clinical Interventions in Aging 2008:3(1) 121-129.

Iranmanesh et al., Age and Relative Adiposity are Specific Negative Determinants of the Frequency and Amplitude of Growth Hormone (GH) Secretory Bursts and the Half-Life of Endogenous GH Healthy Men; Journal of Clinical Endocrinology and Metabolism; vol. 73, No. 5; pp. 1081-1088, 1991.

Isidori et al.; A Study of growth hormone release in man after oral administration of amino acids; Current Medical Research and Opinion; vol. 7, No. 7, 1981; pp. 475-481.

Karlsson et al.; Effects of growth hormone treatment on the leptin system and on energy expenditre in abdominally obese men; European Journal of Endocrinology (1998) 138 408-414.

Kraemer et al.; Chronic Resistance training in women potentiates growth hormone in vivo bioactivity: characterization of molecular mass variants; Am. J. Physiol Endocriol Metab 291: E1177-E1187, 2006.

Lambert et al.; Failure of Commercial Oral Amino Acid Supplements to Increase Serum Growth Hormone Concentrations in Male Body-Builders; International Journal of Sport Nutrition, 1993, 3, 298-305.

Legakis et al.; Human Galanin Secretion is Increased Upon Normal Exercise Test in MiddleAge Individuals; Endocrine Research 26(3), 357-365 (2000).

Maccario et al.; Relationships between IFG-I and age, gender, body mass, fat distribution, metabolic and hormonal variables in obese patients; International Journal of Obesity (1999) 23, 612-618.

Makimura et al.; The relationship between reduced testosterone, stimulated growth hormone secretion and increased carotid inima-media thickness in obese men; Clin Endocrinol (Oxf)Nov. 2010; 73(5): 622-629.

Menagh et al.; Growth Hormone Regulates the Balance Between Bone Formation and Bone Marrow Adiposity; JBMR; vol. 25, No. 4, Apr. 2010, pp. 757-768.

Merimee et al.; Arginine-Initiated Release of Human Growth Hormone; TheNew England Journal of Medicine; Jun. 26, 1969; pp. 1434-1438.

Nindl et al.; Growth hormone pulsatility profile characteristics following acute heavy resistance exercise; J. Appl Physiol p. 163-172, 2001.

O'Connor et al.; Interrelationships of Spontaneous Growth Hormone Axis Activity, Body Fat, and Serum Lipids in Healthy Elderly Women and Men; Metabolism, vol. 48, No. 11 (Nov.), 1999: pp. 1424-1431.

Papadakis et al.; Effect of growth hormone replacement on wound healing in healthy older menWould Repair and Regeneration Oct.-Dec. 1996; pp. 421-425.

Papadakis et al.; Growth Hormone Replacement in Healthy Older Men Improves Body Cmposition but Not Functional Ability; Ann Intern Med. 1996; 124: 708-716.

Pasquali et al.; Hormones and pathophysiology of obesity; Hormones and Obesity; 2001 pp. 920.

Pelsers et al.; Influence of Gender in Growth Hormone Status in Adults: Role of Urinary Growth Hormone; Clinical Chemistry 45, No. 3, 1999, pp. 443-444.

Perry, Horace M. III; The Endocrinology of Aging; Clinical Chemistry 45:8B) 1369-1376 (1999).

Rubin et al.; New anabolic therapies in osteoporosis; Current Opinon in Reeumatology 2002, 14:433-440.

Rudman et al.; Effects of Human Growth Hormone in Men over 60 Years Old; The New England Journal of Medicine; vol. 323, Jul. 5, 1990; 6 pages.

Russell et al. Free Triiodothyronine has a distinct circadian rhythm that is delayed but parallels thyrotropin levels; J. Endocrin Metab. Mar. 25, 2008; 22 pages.

Su et al.; Insulin-like growth factor 1 and hair growth;1999 Dermatology Online Journal; 20 pages.

Suminski et al.; Acute Effect of Amino Acid Ingestion and Resistance Exercise on Plasma Growth Hormone Concentration in Young Men; International Journal of Sport Nutrition, 1997, 7, 4860.

Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488, 2002.

Vance, Mary L.; Growth Hormone for the Elderly?; The New England Journal of Mdicine; Jul. 5, 1990; pp. 52-54.

White et al.; Effects of an Oral Growth Hormone Secretagogue in Older Adults; J. Clin Endocrin Metab.; 2009; 29 pages.

Zouboulis et al.; Intrinsische Hautalterung; Eine kritische Bewertung der Rolle der Hormone; Hautt 2003 54: 825-832.

* cited by examiner

METHODS FOR IMPROVING THYROID FUNCTION IN A SUBJECT

TECHNICAL FIELD

Embodiments of the invention generally relate to methods for increasing improving thyroid function in healthy human beings.

BACKGROUND

Thyroid hormones are critical for normal growth and development and for maintaining metabolic homeostasis. Yen (2001) Physiol. Rev. 81(3):1097-126. Circulating levels of thyroid hormones are tightly regulated by feedback mechanisms in the neuroendocrine axis (i.e., the HPT axis). Thyroid hormones exert profound effects on cardiac function, body weight, metabolism, metabolic rate, body temperature, cholesterol, bone, muscle, and behavior.

Subclinical thyroid diseases (e.g., subclinical hyperthyroidism and subclinical hypothyroidism) are common clinical entities that encompass mild degrees of thyroid dysfunction. The clinical significance of mild thyroid under-activity is uncertain, and therefore there is considerable controversy over the appropriateness of diagnostic testing and possible treatment of this condition. Cooper (2012) Lancet 379(9821): 1142-54; Wilson & Curry (2005) AAFP 72(8). Subclinical hypothyroidism is typically defined as a serum thyroid-stimulating hormone (TSH) concentration above the statistically defined lower limit of the reference range, 0.45 to 4.50 µU/mL (0.45 to 4.50 mU/L), when serum free $T_4$ thyroxine concentration are within its reference range. Subclinical hypothyroidism is associated with progression to overt disease. See, e.g., Wilson & Curry (2005).

Estimates of the incidence of subclinical hypothyroidism range between 3-8%. The incidence of subclinical hypothyroidism steadily increases with age, and it is more common in women than in men. Older adults are twice as likely to develop hypothyroidism as younger adults, the condition is commonly accompanied by symptoms including, for example, constipation, weight gain, dry and itchy skin, impaired cognitive function, and intolerance to cold.

Somatostatin (also known as growth hormone-inhibiting hormone (GHIH)) is a peptide hormone that regulates the endocrine system and affects neurotransmission and cell proliferation via its interaction with G-protein-coupled receptors and inhibition of the release of secondary hormones. For example, in the anterior pituitary gland, somatostatin inhibits the release of TSH and growth hormone.

It is well-established that intravenous (IV) administration of some amino acids results in significant inhibition of somatostatin; indeed this type of diagnostic testing for human growth hormone deficiency (another hormone regulated in part by somatostatin) (Merimee T J et al. N Engl J Med 1969;280:1434-1438; Alba-Roth J et al. J Clin Endocrinol Metab 1988;67:1186-1189). Other amino acids, such as methionine, phenylalanine, lysine, histidine, and ornithine have also led to marked increases in hGH (Alba-Roth, Muller, Schopohl, & von Werder, 1988; Chromiak & Antonio, 2002; Gourmelen, M., M. Donnadieu, et al. (1972) Ann Endocrinol (Paris) 33(5): 526-528).

Determination of an effective and safe oral functional blend that improves thyroid function in the general population with sub-clinical thyroid function is important to determine.

Symptoms such as cold hands and feet, sensitivity to cold, headaches, sleeplessness, coarse skin, swollen eyes, fragile nails, joint aches, constipation, fatigue, croaky voice, and dizziness are associated with subclinical hypothyroidism, and could be treated by improving thyroid function.

It would be desirable to provide a nutritional supplement for improving thyroid function, in particular an amino acid-containing composition that is well tolerated having the result of increasing or improving thyroid function in those individuals whose thyroid function has slowed as a function of increasing age (sub-clinical hypo-thyroid function) or otherwise desire thyroid support.

BRIEF SUMMARY OF THE INVENTION

The present invention is a nutritional supplement and method of using the same. It is a novel amino acid-containing composition, which, taken orally, stimulates improves thyroid function in healthy humans.

A particular embodiment of the present disclosure relates to an oral nutritional supplement that includes the amino acids l-lysine, l-arginine, oxo-proline, and one of either cysteine or glutamine. The amino acids may be delivered as non-toxic salts thereof, effective complexes thereof; stable chelates thereof, active esters thereof, functional derivatives thereof, and mixtures thereof which are effective to improve thyroid function in the general population.

Another particular embodiment relates to an oral nutritional supplement that consists essentially of l-lysine HCl, l-arginine HCl, oxo-proline, N-acetyl-1-cysteine, l-glutamine, and schizonepeta (aerial parts) powder.

Other embodiments are drawn to methods of improving thyroid function in humans that include orally administering the disclosed nutritional supplement to a healthy human being.

DETAILED DESCRIPTION OF THE INVENTION

The present invention relates to a nutritional supplement for use by a human being. The present invention is drawn to a nutritional supplement and method of using the same. The nutritional supplement is an amino acid-containing composition, which, taken orally, improves thyroid function in healthy volunteers. For example, the nutritional supplement may prevent the occurrence or reduce the severity of at least one symptom associated with hypothyroidism, including for example and without limitation, cold hands and feet, sensitivity to cold, headaches, sleeplessness, coarse skin, swollen eyes, fragile nails, joint aches, constipation, fatigue, croaky voice, and dizziness. The supplement of the present invention works as a dietary supplement by assisting the body's own ability to improve thyroid function naturally in a manner that is safe and effective, as well as being affordable.

A particular embodiment of the present disclosure relates to an oral nutritional supplement that includes l-lysine, l-arginine, oxo-proline, and one of either cysteine or glutamine. The supplement may additionally include both cysteine and glutamine and/or schizonepeta powder. In particular embodiments, a functional dosage includes the l-arginine at a level between 0.1-6 moles and the oxo-proline between 0.1-8 moles, and/or the l-lysine in an amount between 0.1-12 moles. The cysteine and/or glutamine may be contained at a level between 0.001-6 moles. The cysteine can be n-acetyl L-cysteine and the glutamine may be l-glutamine. The amino acids may be delivered as non-toxic salts thereof, effective complexes thereof, stable chelates thereof, active esters thereof, functional derivatives thereof, and mixtures thereof which are effective to increase hGH levels in the general population. The nutritional supplement may be present in an amount of 2.9 grams. The nutritional supplement may be in any acceptable and known oral formulation, such as powder, tablet, capsule, liquid, or wafer form.

Another particular embodiment relates to an oral nutritional supplement that consists essentially of 1-lysine HCl, 1-arginine HCl, oxo-proline, N-acetyl-l-cysteine, 1-glutamine, and schizonepeta (aerial parts) powder. In particular embodiments, a functional dosage includes the 1-arginine HC1 at a level between 0.1-6 moles and the oxo-proline between 0.1-8 moles, and/or the 1-lysine HCl in an amount between 0.1-12 moles. The n-acetyl L-cysteine and/or 1-glutamine may be contained at a level between 0.001-6 moles. In another particular embodiment, a functional dosage includes the 1-arginine HCl at a level between 2.5-4.5 moles and the oxo-proline between 4-6 moles, and/or the 1-lysine HCl in an amount between 7-9 moles. The n-acetyl L-cysteine and/or 1-glutamine may be contained at a level between 0.001-0.5 moles. The nutritional supplement may be in any acceptable and known oral formulation, such as powder, tablet, capsule, liquid, or wafer form.

Other embodiments are drawn to methods of improving thyroid function in humans that include orally administering the disclosed nutritional supplement to a healthy human being. As used herein, "healthy human being" means a human being without any physiological deficiency in thyroid function, but rather has symptoms of sub-clinical hypothyroid function. Particular embodiments of the invention relate to oral administration of the disclosed nutritional supplement to a human that is at least 30 years old. The nutritional supplement may be administered from one to three times daily or, alternatively, may be administered every other day, or may be administered once a week. In particular embodiments, the nutritional supplement may be administered on an empty stomach.

In accordance with the "consist essentially of" and "consisting essentially of" language, the nutritional supplement of the third embodiments is essentially limited to the aforementioned ingredients and does not include any additional active ingredients intended to add nutritional content (e.g., vitamins, minerals, etc.), but may include additional ingredients not intended to add nutritional content such as ingredients intended to fulfill a non-nutritional purpose (e.g., coloring, fillers, flavoring, an ingredient for maintaining the structural form, etc.).

Each ingredient of the nutritional supplement of the present invention may be prepared in accordance with any method known to one of ordinary skill in the art. Alternatively, each ingredient may be obtained in a fully prepared from a commercially available source.

The nutritional supplement of the present invention may be in any suitable oral administration form, including but not limited to: a chewable form, a liquid form, a spray form, a capsule form, a suppository form, dissolvable wafer, and a powder form.

Irrespective of the structural form of the nutritional supplement, the ingredients of the nutritional supplement may be distributed homogeneously or non-homogeneously within the nutritional supplement.

The nutritional supplement of the present invention may be ingested on a regular basis, such as a daily or weekly intake at a dosage tailored to an individual's needs; i.e., the nutritional supplement is to be taken regularly as multiples (1×, 2×, etc.) of the structural units (pills, tablets, capsules, liquid dose, etc.) in accordance with the needs of the individual. Alternatively, the nutritional supplement of the present invention may be ingested on an as-needed basis at a dosage tailored to the individual's needs. Medical or nutritional counseling may be beneficial for arriving at a desirable or optimal dosage tailored to the individual's needs.

The combination of types of amino acids, mass ranges, and specific formulations have been selected to be synergistically balanced and of adequate quantity to achieve the desired physiological effect, namely, thyroid support. Improper combinations of the amino acids may be ineffective. The component amino acids are synergistic in the sense that several of them when combined together, synergistically improve thyroid function. The combination was also chosen to reduce or inhibit chemical combination or reaction between the amino acids.

EXAMPLES

Methods: This cross-over, placebo controlled, double-blind study involved 16 healthy subjects [12 males, 4 females; 9 Caucasian, 6 African American, 1 other; mean age=32±14 years; body mass index=26.4 ±5.0 ranging from 19.1 to 36.8 $kg/m^2$]. Each subject reported to the Inpatient Unit on two occasions one week apart. After an overnight fast, subjects had an IV line placed and baseline bloods samples were drawn at −30, −15, and 0 minutes. Subjects were then asked to swallow the capsules of the test supplement or an identical looking placebo.

The administered supplement is a novel 2.9 g/dose blend of 1-lysine HCl, 1-arginine HCl, oxo-proline, N-acetyl-l-cysteine, 1-glutamine, and schizonepeta (aerial parts) powder. Blood was drawn at regular intervals for 120 minutes after administration. Baseline and 120 minute time points were assayed for triiodothyronine (T3).

As daily circadian levels of T3 naturally decrease during the morning hours, at which the current trial was scheduled, it was not surprising that placebo levels between the baseline and 120 minute time points decreased by −6.10 ng/dL (106 to 100 ng/dL, P=0.01). In contrast, the SeroVital™ group exhibited a deceased reduction in T3 by nearly one-half over the same time course, −3.3 ng/dL (101-97.3 ng/dL, NS), which was not a significant reduction compared to baseline, as was the reduction in the placebo group. These results affirm that supportive function of SeroVital in thyroid function.

This study is distinct in that it had a broad range of ages and BMI's and included both genders. An additional advantage of this study of the novel amino-acid containing blend is that it contained a placebo control group and was randomized and double-blinded.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method for maintaining baseline thyroid function in a healthy human being, the method comprising
    orally administering an effective amount of a nutritional supplement to the healthy human being, the nutritional supplement consisting essentially of:
        about 1 mmol L-arginine;
        about 1 mmol Oxo-proline;
        about 2 mmol L-lysine;
        about 1.5 μmol N-acetyl L-cysteine;
        about 2 μmol L-glutamine; and
        about 125 μg Schizonepta (aerial parts) powder.
2. The method according to claim 1, wherein the method comprises orally administering the nutritional supplement in an amount of about 2.9 grams.

3. The method according to claim 1, wherein the nutritional supplement is in a unit dosage form of a powder, tablet, capsule, liquid, or wafer.

4. The method according to claim 1, wherein the nutritional supplement is administered from one to three times daily.

5. The method according to claim 1, wherein the nutritional supplement is administered once a week.

6. The method according to claim 1, wherein the nutritional supplement is administered to the healthy human being with an empty stomach.

7. The method according to claim 1, wherein the healthy human being is at least 30 years old.

8. The method according to claim 1. wherein the method comprises orally administering the nutritional supplement in an amount of about 2.9 grams.

9. The method according to claim 1, wherein the nutritional supplement is in a unit dosage form of a powder, tablet, capsule, liquid, or wafer.

10. The method according to claim 1, wherein the nutritional supplement is administered from one to three times daily.

11. The method according to claim 1, wherein the nutritional supplement is administered once a week.

12. The method according to claim 1. wherein the nutritional supplement is administered to the healthy human being with an empty stomach.

13. The method according to claim 1, wherein the healthy human being is at least 30 years old.

14. A method for maintaining baseline thyroid function in a healthy human being, the method comprising:
orally administering an effective amount of a nutritional supplement to the healthy human being, the nutritional supplement consisting essentially of 3.44 mmol L-arginine; 5.30 mmol Oxo-proline; 8.21 mmol L-lysine; 6.13 µmol N-acetyl L-cysteine; 6.84 µmol L-glutamine; and 0.50 mg Schizonepta (aerial parts) powder.

* * * * *

UNITED STATES PATENT AND TRADEMARK OFFICE
CERTIFICATE OF CORRECTION

| | |
|---|---|
| PATENT NO. | : 8,815,311 B2 |
| APPLICATION NO. | : 13/623116 |
| DATED | : August 26, 2014 |
| INVENTOR(S) | : Amy L. Heaton, Mitchell K. Friedlander and Dennis Gay |

It is certified that error appears in the above-identified patent and that said Letters Patent is hereby corrected as shown below:

On the title page:
In ITEM (71) Applicant:   change "Inc.," to --LLC,--
In ITEM (56) References Cited
    PUBLICATIONS
    Page 1, 1st column, 3rd line of the
        9th entry (line 62),   change "11861189." to --1186-1189.--
    Page 1, 2nd column, 4th line of the
        1st entry (line 4),   change "695704;" to --695-704;--
    Page 1, 2nd column, 1st line of the
        2nd entry (line 5),   change "premenopausal" to --pre-menopausal--
    Page 1, 2nd column, 2nd line of the
        2nd entry (line 6),   change "fora" to --for a--
    Page 1, 2nd column, 3rd line of the
        2nd entry (line 7),   change "insulinlike" to --insulin-like--
    Page 1, 2nd column, 1st line of the
        6th entry (line 17),   change "tissre" to --tissue--
    Page 1, 2nd column, 2nd line of the
        6th entry (line 18),   change "191302." to --191-302.--
    Page 1, 2nd column, 1st line of the
        10th entry (line 30),   change "HormoneReleasing" to --Hormone-Releasing--
    Page 1, 2nd column, 2nd line of the
        12th entry (line 35),   change "2039." to --20-39.--
    Page 1, 2nd column, 2nd line of the
        13th entry (line 37),   change "Insulinlike" to --Insulin-like--
    Page 1, 2nd column, 2nd line of the
        17th entry (line 50),   change "InsulinLike" to --Insulin-Like--
    Page 2, 1st column, 3rd line of the
        2nd entry (line 11),   change "GH Healthy" to --GH in Healthy--

Signed and Sealed this
Twenty-ninth Day of September, 2015

Michelle K. Lee
*Director of the United States Patent and Trademark Office*

CERTIFICATE OF CORRECTION (continued)
U.S. Pat. No. 8,815,311 B2

On the title page:
In ITEM (56) References Cited
    PUBLICATIONS

| | |
|---|---|
| Page 2, 1st column, 2nd line of the 4th entry (line 18), | change "expenditre" to --expenditure-- |
| Page 2, 1st column, 3rd line of the 5th entry (line 22), | change "Endocriol" to --Endocrinol-- |
| Page 2, 1st column, 2nd line of the 7th entry (line 28), | change "MiddleAge" to --Middle-Age-- |
| Page 2, 2nd column, 2nd line of the 3rd entry (line 8), | change "menWould" to --men, Would-- |
| Page 2, 2nd column, 2nd line of the 4th entry (line 11), | change "Cmposition" to --Composition-- |
| Page 2, 2nd column, 2nd line of the 5th entry (line 14), | change "920." to --9-20.-- |
| Page 2, 2nd column, 2nd line of the 7th entry (line 19), | change "45:8B)" to --45:8(B)-- |
| Page 2, 2nd column, 1st line of the 10th entry (line 25), | change "distrinct" to --distinct-- |
| Page 2, 2nd column, 2nd line of the 10th entry (line 26), | change "J. Endocrin" to --J. Clin Endocrin-- |
| Page 2, 2nd column, 3rd line of the 12th entry (line 32), | change "4860." to --48-60.-- |
| Page 2, 2nd column, 2nd line of the 14th entry (line 38), | change "Mdicine;" to --Medicine;-- |
| Page 2, 2nd column, 2nd line of the 16th entry (line 42), | change "Hautt" to --Hautarzt-- |

In the claims:

| | | | |
|---|---|---|---|
| CLAIM 8, | COLUMN 5, | LINE 14, | change "claim 1." to --claim 14,-- |
| CLAIM 9, | COLUMN 5, | LINE 17, | change "claim 1," to --claim 14,-- |
| CLAIM 10, | COLUMN 6, | LINE 1, | change "claim 1," to --claim 14,-- |
| CLAIM 11, | COLUMN 6, | LINE 4, | change "claim 1," to --claim 14,-- |
| CLAIM 12, | COLUMN 6, | LINE 6, | change "claim 1." to --claim 14,-- |
| CLAIM 13, | COLUMN 6, | LINE 9, | change "claim 1," to --claim 14,-- |
| CLAIM 14, | COLUMN 6, | LINE 15, | change "3.44mmol" to --3.44 mmol-- |